(12) United States Patent
Browdie

(10) Patent No.: US 6,310,036 B1
(45) Date of Patent: Oct. 30, 2001

(54) HIGH STRENGTH, BIO-COMPATIBLE TISSUE ADHESIVE AND METHODS FOR TREATING VIGOROUSLY BLEEDING SURFACES

(75) Inventor: David A. Browdie, Fargo, ND (US)

(73) Assignee: Last Chance Tissue Adhesives Corporation, Golden Valley, MN (US)

( * ) Notice: Subject to any disclaimer, the term of this patent is extended or adjusted under 35 U.S.C. 154(b) by 0 days.

(21) Appl. No.: 09/227,400

(22) Filed: Jan. 9, 1999

(51) Int. Cl.[7] .......................... A01N 37/18; A61K 38/00; A61K 38/17; A61K 39/00; C07K 1/00
(52) U.S. Cl. .................................. 514/2; 514/12; 530/300; 530/350; 530/324; 530/345; 530/356; 530/362; 424/184.1; 424/185.1; 424/193.1; 424/194.1; 424/422; 424/443
(58) Field of Search .................................... 514/12, 2, 21; 128/898; 530/324, 300, 350, 345, 356, 362; 424/422, 184.1, 185.1, 193.1, 194.1, 443; 606/213, 214, 215; 602/904

(56) References Cited

U.S. PATENT DOCUMENTS

| | | |
|---|---|---|
| 3,438,374 | 4/1969 | Falb et al. . |
| 3,483,870 | 12/1969 | Coover et al. . |
| 3,995,641 | 12/1976 | Kronenthal et al. . |
| 4,414,976 | 11/1983 | Schwarz et al. . |
| 4,804,691 | 2/1989 | English et al. . |
| 4,909,251 | 3/1990 | Seelich . |
| 5,209,776 | 5/1993 | Bass et al. . |
| 5,219,328 | 6/1993 | Morse et al. . |
| 5,254,113 | 10/1993 | Wilk . |
| 5,292,333 | 3/1994 | Johnson . |
| 5,292,362 * | 3/1994 | Bass et al. . |
| 5,350,798 | 9/1994 | Linden et al. . |
| 5,385,606 | 1/1995 | Kowanko . |
| 5,395,923 | 3/1995 | Bui-Khac et al. . |
| 5,401,819 | 3/1995 | Byerley et al. . |
| 5,407,671 | 4/1995 | Heimburger et al. . |
| 5,445,597 | 8/1995 | Clark et al. . |
| 5,464,471 | 11/1995 | Whalen et al. . |
| 5,571,080 | 11/1996 | Jensen . |
| 5,583,114 | 12/1996 | Barrows et al. . |
| 5,669,934 | 9/1997 | Sawyer . |
| 5,690,675 | 11/1997 | Sawyer et al. . |
| 5,749,895 | 5/1998 | Sawyer et al. . |
| 5,749,968 | 5/1998 | Melanson et al. . |
| 5,788,662 | 8/1998 | Antanavich et al. . |
| 5,791,352 | 8/1998 | Reich et al. . |
| 5,800,373 | 9/1998 | Melanson et al. . |
| 5,804,428 | 9/1998 | Edwardson et al. . |
| 5,814,022 | 9/1998 | Antanavich et al. . |
| 5,824,015 | 10/1998 | Sawyer . |
| 5,830,700 | 11/1998 | Irani . |

FOREIGN PATENT DOCUMENTS

WO 97/24090  7/1997  (WO) .

\* cited by examiner

Primary Examiner—Avis M. Davenport
(74) Attorney, Agent, or Firm—Oppenheimer Wolff & Donnelly LLP

(57) ABSTRACT

Disclosed is a novel tissue adhesive technology comprising a combination of ultrasonically treated proteins including collagen and albumin which form a viscous material that develops adhesive properties when chemically cross-linked. A novel new cross-linking agent with surprisingly stable properties was developed in association with the tissue adhesive described and claimed herein and is considered to be within the scope of the present invention. This new cross-linking agent is a product of reacting glutaraldehyde with amino acids or peptides and allowing the reaction to proceed to completion. This chemical cross-linker is mixed with the ultrasonically treated proteins, allowed to react for a pre-determined time, then used to seal large surface areas of vigorously bleeding tissues including, but not limited to, the liver, lungs and major vascular systems in patients with and without bleeding disorders. This same tissue adhesive has proven to work well in sealing suture sites to prevent leakage.

12 Claims, No Drawings

HIGH STRENGTH, BIO-COMPATIBLE TISSUE ADHESIVE AND METHODS FOR TREATING VIGOROUSLY BLEEDING SURFACES

BACKGROUND

The present invention relates generally to adhesives, more specifically it relates to medical adhesives, and particularly it relates to tissue adhesives which exhibit high bio-compatibility, excellent tensile properties, are bio-absorbable, do not interfere with the healing processes and are easily applied to various tissues. The present invention is also particularly well suited for controlling complex, vigorous bleeding emanating from large surface areas, specifically the visceral organs, lungs and the vascular system.

The use of adhesive compounds in wound sealing and hemorrhage control dates back to the sixteenth century. Early sealants consisted of rosewater, turpentine and eggs and were used in conjunction with ligatures. *Biologic and Synthetic Polymer Networks,* Ed. O. Kramer, Elsevier Applied Science, New York (1988). While such techniques offered marked improvement over cautery, little effort was made to advance the art until the Spanish Civil war when plasterized cotton was introduced. Leo Mandelkern, *An Introduction to Macromolecules* 2nd ed.; Springer Verlag, New York (1983). Early cotton-based adhesives were little more than surgical packings and could not control large, profusely bleeding visceral surfaces.

Subsequent wars brought new experiments with adhesives to aid in controlling the massive, vigorously bleeding hemorrhages associated with battlefield injuries. In the 1940s, trauma surgeons began experimenting with fibrin sealants, however, these did not possess the strength required to adequately control vigorous bleeding wounds and W.W. II field hospitals returned to plasterized cotton. Turner Alfrey et al., *Organic Polymers,* Prentice Hall, New Jersey (1967). Technological advances in polymer chemistry led to the development of cyanoacrylates that were first used as tissue adhesives in the Vietnam war. Since that time, moderate advances have been made in the development of modern tissue adhesives, but none have adequately addressed the technical and biological complexities associated with vigorous bleeding homeostasis.

Severe traumatic injuries result in massive intra-abdominal hemorrhages in approximately 10 to 25% of cases. Uncontrolled bleeding and transfusion-associated complications make up the majority of deaths in these patients. The current recommended standard of care for treating intra-abdominal bleeding is a process called packing which utilizes pressure and nylon gauze to contain the blood flow. A. Sauaia, et al., *Epidemiology of Trauma Deaths: a Reassessment,* Journal of Trauma (February 1995). However, in spite of advances in nearly every other branch of medicine, mortality rates associated with severe abdominal trauma remain high. Traditional methods of tissue closure including tapes, sutures and staples are completely inadequate when the effected area is the surface of a visceral organ that has been severely lacerated or ruptured.

Tapes, sutures and staples fail to assure fluid-tight closures and often require surgical removal even when used as clinically indicated. These disadvantages are further exacerbated by the scarring, additional tissue damage and inflammation often associated with such techniques. The exposed tissue at the suture site can become infected requiring frequent cleaning and treatment with topical as well as systemic antibiotics. Another significant drawback to sutures, staples and tapes is their inability to be used in combination with microsurgical techniques. Consequently, the development of a versatile bio-compatible, non-toxic tissue adhesive, suitable for controlling vigorous bleeding over large surface areas, that has high adhesive strength and excellent tensile properties would constitute a major medical and technical advance.

Multiple factors must be considered when evaluating candidate tissue adhesives. The most important of these include bio-compatibility, resistance to fracture, pliability, adhesive strength, ease of application, and rapid curing time. Materials which possess ideal bio-compatibility are immunologically inert, do not interfere with wound healing, do not induce strictures or scars, are bio-absorbable and completely non-toxic. Due to these demanding criteria, it has been extremely difficult to find an ideal material.

Various forms of wound sealant technologies exist including fibrin sealants, gelatin resorcin aldehyde adhesives, albumin based tissue adhesives, acrylates, tissue welding technologies and argon beam electro-coagulation. In the United States, fibrin, acrylate and argon beam electro-coagulation have received the most attention. None of these technologies adequately control the complex, vigorous bleeding associated with severe internal injuries.

Fibrin tissue adhesives have attracted considerable attention due to the high bio-compatibility associated with fibrin monomers. Fibrin tissue adhesives are administered as two components and work by forming an artificial fibrin clot over the effected area. The fibrinogen and Factor XIII component is delivered to the wound site followed by a thrombin and calcium ion solution which initiates the conversion of fibrinogen into fibrin monomers. Fibrin tissue adhesives exhibit relatively weak tissue binding properties, have a fairly long set-up time and are not suitable for use in treating large, aggressively bleeding surfaces. The amount of fibrin required to produce a satisfactory adhesive requires multiple blood donors which increases the risk of transmitting blood borne diseases. These risks will be significantly reduced as recombinant coagulation factors and fibrin become more readily available.

Fibrin based tissue adhesives have been described in a number of U.S. patents, the most relevant of those include U.S. Pat. Nos. 4,414,976, 4,909,251, 5,219,328, 5,395,923, 5,407,671, 5,464,471, 5,804,428 and 5,814,022. U.S. Pat. No. 4,414,976 describes the basic fibrin based tissue sealant and discloses the fundamental theory associated with its biological activity. The remaining patents cited above are primarily directed at novel means for delivering fibrin and the required clotting agents to the wound site in a convenient fashion making the use of this tissue adhesive more acceptable to physicians. U.S. Pat. No. 5,407,671 addresses the transmission of blood borne pathogens and is directed at minimizing this inherent risk, while U.S. Pat. No. 5,464,471 is directed to recombinant forms of fibrin and application techniques thereof. However, none of these patents discuss the use of a fibrin based tissue adhesive for controlling vigorous bleeding, tissues.

Gelatin Resorcin Aldehyde Tissue Adhesives (GRATA) are currently available in Germany for use in conjunction with cardiovascular surgery. These compounds are generally used as reinforcement or leathering agents on fragile tissues. Gelatin Resorcin Aldehyde Tissue Adhesives are composed of heated gelatin that is mixed in situ with a cross-linking agent such as glutaraldehyde or formaldehyde. In general, GRATAs are relatively easy to apply and have moderately good adhesive qualities. However, GRATA do not possess adhesive qualities sufficient to seal large areas of vigorously bleeding tissues and there are reports of post surgical inflammation in rabbits indicating problems with biocompatibility. U.S. Pat. No. 5,292,333 describes a more recent GRATA development but does not suggest that the claimed tissue adhesive would be suitable for sealing large surface areas of vigorously bleeding tissues. The examples described therein are limited to vascular grafts.

U.S. Pat. No. 5,583,114 discloses an albumin based tissue adhesive prepared using an alkaline solution of human serum albumin that is cross-linked with polyethylene glycol. The resulting tissue adhesive is intended for use as an adjunct or replacement of sutures, stables, tapes and/or bandages. Other proposed uses include post-surgical applications to reduce tissue adhesions, sealing tissues to prevent or control blood or other fluid leaks at suture or staple sites and for controlling leaks in the pulmonary system. Treating large surface areas of vigorously bleeding tissues is not described.

Acrylates are semi-crystalline compounds that tend to fracture under stress which can result in wound healing inhibition. The cyanoacrylates have been exhaustively studied and is the most successful acrylate class used as tissue adhesives. N-isobutyl and N-butylcyanoacrylate were initially selected for development after animal tests suggested that these compounds demonstrated superior tissue adhesiveness and minimal tissue inflammation. N-butylcyanoacrylate is available outside the U.S. for human applications and as an approved veterinary compound within the U.S.

Acrylate tissue adhesives require a dry field for application, fragment easily, are non-bio-absorbable and the polymerization can be extremely exothermic. It has also been reported that the ridged acrylate polymer is nonporous and prevents cell communication and movement which significantly retards would healing. This combination of adverse physical qualities has significantly limited the use of acrylate tissue adhesives with internal applications. Several U.S. patents have been granted in this area of tissue adhesive research including U.S. Pat. Nos. 3,483,870, 3,995,641, and 5,350,798. The compounds described in these patents are primarily intended for sealing superficial cuts and wounds and not intended to control the vigorous bleeding associated with massive injuries to vital organs.

Tissue welding is an area where significant research and development has been focused. Numerous U.S. patents have been issued in this area including four assigned to Fusion Medical Technologies, Inc. of Mountain View, Calif. U.S. Pat. No. 5,669,934 describes the use of a preformed sheet made of collagen, gelatin and mixtures thereof combined with a plastisizer which is sealed to the injured tissue using radio frequencies between 20 and 120 watts. The principle application for this device is the repair of severed and torn tissues including blood vessels, ducts, muscle, fascia, tendon and bone. Although bleeding is often a collateral consequence of injuries to these tissues, control of vigorous bleeding over large surface areas is not disclosed in the '934 patent.

Fusion Technologies U.S. Pat. Nos. 5,690,675, 5,749,895 and 5,824,015 also use patches made from collagen and/or gelatin which are used in conjunction with a device which emits sufficient radio frequency or optical energy to literally weld the patch into place. These devises are particularly well suited for repairing severed tissues, veins, nerves, tendons and muscle where strong, rapid structural repair is required. However, this process does not lend itself to sealing large vigorously bleeding surfaces and such use is not described in the above cited patents.

A hybrid technology has been developed and is disclosed in U.S. Pat. Nos. 5,209,776 and 5,292,362 (Bass patents). These patents describe the development of a tissue adhesive that is principally intended to be used in conjunction with a laser to weld severed tissues and/or prosthetic material together or to form a water tight seal for tissues or prosthetic devices. However, in some cases the tissue adhesive described will spontaneously weld tissues together without the use of an external energy source. The Bass patents disclose an adhesive comprising a first component of fibrous and/or globular proteins, preferably collagen and albumin, which can be used either together or separately and combined with a second component that is made of proteoglycans, glycoproteins, saccharides, polyalcohols, proteins, gels, or similar compounds. The second component provides a matrix, or foundation, for the first component to complex with and form a gel or solution. The resulting gel or solution can be subsequently modified with viscosity agents, bonding enhances and polar dyes which alter the tissue bonding effects when used in conjunction with a laser.

In the Bass patents neither the collagen nor the albumin are ultrasonically modified and the use of both proteins is not required. In the present invention the albumin and collagen are ultrasonically treated and are used together in a synergistic fashion. Furthermore, there is no chemical cross-linking of the proteins used in the Bass patents. Equally important is that neither Bass patent discloses the use of the adhesive system described for controlling large surface areas of complex, vigorously bleeding tissues.

Argon beam high electro-coagulation is a physical technique, not a tissue adhesive per se. High frequency energy is applied directly to the tissue surface causing the rapid evaporation of water resulting in coagulation. However, this process has not proven successful in treating large tissue surface areas and is especially ineffective in patients with coagulopathies.

A number of interesting approached to wound and tissue sealing are described in U.S. Pat. Nos. 4,804,691, 5,445,597, 5,571,080, 5,788,662, and 5,830,700. These include recombinant hybrid proteins, fibrin/thrombin dispensing devises, adhesive pads, and novel polyester compounds. However, none of these devices adequately address the need for a tissue adhesive suitable for emergency use involving traumatic injuries resulting in large surfaces of complex, vigorously bleeding tissues.

The preceding review of the prior art demonstrates the dearth of technical advances in controlling severe bleeding situations using bio-compatible adhesives. In the four centuries since crude sealants consisting of rosewater, turpentine and eggs were first introduced the only significant advance has been Trueta's development of plasterized cotton over 100 years ago. The present invention offers the first acceptable alternative to crude packing techniques currently practiced in trauma centers throughout the world and represents a novel, technically significant and life savings advance in the medial sciences.

It is therefore the object of the present invention to produce a tissues adhesive that is bio-compatible, bio-absorbable, does not interfere with tissue healing, has sufficient adhesive strength to control vigorous bleeding over large surface areas, can be applied rapidly to a variety of tissues and is suitable for use in patients with coagulation disorders.

SUMMARY

The present invention is directed to a composite tissue bonding and tissue modifying technology which fulfills the needs expressed above. This novel tissue adhesive technology comprises a combination of ultrasonically treated proteins including collagen and albumin which form a viscous material that develops adhesive properties when chemically cross-linked.

A novel new cross-linking agent with surprisingly stable properties was developed in association with the tissue adhesive described and claimed herein and is considered to be within the scope of the present invention. This new cross-linking agent is a product of reacting glutaraldehyde with amino acids or peptides and allowing the reaction to proceed to completion. This chemical cross-linker is mixed with the ultrasonically treated proteins, allowed to react for a pre-determined time, then used to seal the large surface areas of vigorously bleeding tissues including, but not limited to, the liver, lungs and major vascular systems in patients with and without bleeding disorders. This same tissue adhesive has proven to work well in sealing suture sites to prevent leakage.

Another surprising and exciting aspect of this invention is the versatility of the base adhesive. When the cross-linked tissue adhesive of the present invention is mixed with magnesium carbonate under alkaline conditions the resulting compound becomes a powerful bone adhesive. This bone adhesive differs from the tissue adhesive in that it is much less malleable upon curing making it ideal for cementing rigid anatomical structures while maintaining the bioabsorbability and high bio-compatibility properties of the base adhesive.

The novel combination of cross-linked fibrous and globular proteins were specifically selected with bio-compatibility in mind. Collagen and albumin are both ubiquitous mammalian proteins that have a long history of medical use with few reported side effects. In studies detailed below, post-mortem examinations up to six months following surgery demonstrated normal healing, no inflammation and uncomplicated resorbtion which is indicative of high the bio-compatibility characteristic of this novel tissue adhesive.

The tissue bonding materials described in this patent include novel semi-liquid tissue adhesives, non-malleable bone adhesive, surprisingly stable and effective cross-linking agents and combinations thereof. These and other features, aspects and advantages of the present invention will become better understood with reference to the following description and appended claims.

DETAILED DESCRIPTION

Tissue adhesives formed by the methods of the present invention must possess the adhesive strength necessary to seal a vigorous bleeding tissue sufficiently to allow complete healing with minimal toxic side effects. Tissue adhesives of the present invention which develop a cohesive strength of at least 5 kg/cm$^2$ at five minutes post application with an adhesive bonding strength of at least 1 kg/cm$^2$ can adequately control vigorous bleeding in all body tissues including spleens, livers, lungs, the vascular system and bone.

One embodiment of the present invention is prepared by mixing an ultrasonically treated fibrous protein with ultrasonically treated globular protein, adding a cross-linking agent and allowing the reaction to proceed for 1–3 minutes. The resulting adhesive can then be applied directly to vigorously bleeding tissues including visceral organs.

In the preferred embodiment of the present invention the novel cross-linking agent is first prepared by mixing three parts glutamate solution (3–6 M in distilled water) with one part of a 7% aqueous glutaraldehyde solution. The resulting mixture is allowed to react for 48 hours at room temperature or until no discernible aldehyde signal is detectable using infrared spectroscopy, the solution has turned yellow-brown, pH is approximately 4.5–6.5 and all trace of characteristic aldehyde odor is eliminated. When the fully reacted cross-linking agent is further examined using infrared analysis of aqueous and methanol solutions, a lower range infrared absorption signal is detected which is consistent with an incomplete pyrimidine compound. The importance of this signal in not known and is not intended to limit this invention.

A one percent collagen solution, preferably bovine or porcine collagen, is made in distilled water and sonicated at 0.5 to 1.5 watts/cm$^2$ at 17 kHz to 24 kHz for approximately 12 hours at 6° C. to 10° C. The sonicated solution is then concentrated using cold lyophilization. The final concentration of the collagen solution is between 35% to 45%. A five percent aqueous solution of albumin, preferably human, is processed as the collagen was except that the total sonication time is reduced to approximately two hours. The albumin was then concentrated to 35–45% using cold lyophilization. The resulting collagen and albumin solutions are then mixed in a 1:1 ratio.

The final adhesive is prepared by mixing four to eight parts of the collagen/albumin solution with one part of the cross-linking solution and 0.01% methylene blue. This adhesive can used as a stand alone sealant or in conjunction with tissue patches made from bio-compatible materials.

In yet another embodiment, 0.5 M magnesium carbonate diluted in an 0.5 M aqueous solution of ammonium hydroxide, pH 8, is added to the preferred embodiment of the tissue adhesive in an amount sufficient to give a viscosity suitable for use as a bone adhesive. In another version of this bone adhesive, approximately 9% to 20% by weight of hydroxyapatite was added to in addition to the alkaline magnesium carbonate. Both formulations were equally satisfactory.

Experiments were conducted in vivo using porcine and rabbit models. Test animals were anti-coagulated with intravenous heparin (300 unit/kg) and measured bleeding times (PTT) exceeded 250 seconds. A pig's liver is severely lacerated and the surface disrupted using multiple strokes with a scalpel. This heavily bleeding, flat disrupted surface represents the worst-case scenario for a wound closure agent. The surface of the liver is coated with the tissue adhesive to a thickness of approximately one to three millimeters, and after a short application time, the bleeding is completely stopped. Postmortem studies of tissues from pigs sacrificed at six weeks following the application of the tissue adhesive to vigorously bleeding visceral organs demonstrated minimal adhesions, normal wound healing and ongoing resorbtion of these adhesive materials. Similar results were achieved with rabbits.

In another experiment the abdominal artery of a 145 pound pig is exposed and opened with a 4 mm punch. With no clamping an 12 mm bio-compatible tissue patch coated with the tissue adhesive of the present invention is applied and held in place over the hole. Complete occlusion and sealing is observed when pressure is released.

Following the aortic punch procedure the same anti-coagulated pig has a portion of the lower lobe of a lung surgically removed then re-attached loosely with sutures. Water is poured over the suture area to demonstrate that air is still escaping from the repair site. The present tissue adhesive is then applied to the site to correct this. The wound was completely closed, all bleeding and air leakage was stopped.

To determine whether the present invention would also be suitable for sealing suture lines, braided sutures were coated with the tissue adhesive of the present invention and then used to suture fresh porcine aorta and pulmonary segments together. A control set using braided sutures that were not previously coated with adhesive were also prepared. Next, both groups of sutured tissues were pressurized with water to 200 mm Hg and leakage was compared. Less than 25% of the pre-treated group demonstrated leakage compared with leakage rates of up to 30 cc per minute in 100% of the control group. Ten replicates were used for each group.

Although the present invention has been described in considerable detail with reference to certain preferred versions thereof, other versions are possible. For example, other amino acids and concentrations than 3–5 M glutamate can be used in the preparation of the cross-linking agent. Many different grades and sources of fibrous protein, globular protein, glutaraldehyde, amino acids and polypeptides are acceptable and this adhesive can be used with or without the addition of methylene blue. Bio-compatible tissue patches made from a variety of materials can be used with the present adhesive, or the adhesive may be used in a stand-alone capacity. Therefore, the spirit and scope of the appended claims should not be limited to the description of the preferred versions contained herein.

I claim:

1. A tissue adhesive for controlling vigorously bleeding tissues comprising:
   at least one fibrous protein;
   at least one globular protein; and
   at least one cross-linking agent; wherein
   said at least one fibrous protein and said at least one globular protein are ultrasonically treated prior to application to a mammalian tissue in need thereof.

2. The tissue adhesive of claim 1 wherein the fibrous protein is collagen.

3. The collagen of claim 2 wherein said collagen is selected from the group consisting of human collagen, porcine collagen and bovine collagen.

4. The tissue adhesive of claim 1 wherein the globular protein is albumin.

5. The albumin of claim 4 wherein said albumin is selected from the group consisting of human albumin, porcine albumin and bovine albumin.

6. The tissue adhesive of claim 1 wherein the cross-linking agent comprises glutaraldehyde and a member selected from the group consisting of amino acids, polypeptides and proteins.

7. The cross-linking agent of claim 6 wherein the amino acid is glutamate.

8. The tissue adhesive of claim 1 wherein the ratio of ultrasonically treated fibrous protein to ultrasonically treated globular protein is approximately 1:1.

9. The ultrasonically treated fibrous protein of claim 8 wherein the fibrous protein component comprises an aqueous solution with approximately 35% to 45% collagen.

10. The ultrasonically treated globular protein of claim 8 wherein the globular protein component comprises an aqueous solution with approximately 35% to 45% albumin.

11. The tissue adhesive of claim 1 which develops a cohesive strength of at least 5 kg/cm$^2$ and an adhesive bonding strength of at least 1 kg/cm$^2$ within five minutes post application.

12. The tissue adhesive of claim 1 further comprising approximately 0.01% methylene blue.

* * * * *